US00PP12342P2

(12) United States Plant Patent
Trujillo

(10) Patent No.: US PP12,342 P2
(45) Date of Patent: Jan. 8, 2002

(54) TARO CULTIVAR NAMED 'PAUAKEA'

(75) Inventor: Eduardo E. Trujillo, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/426,393

(22) Filed: Oct. 22, 1999

(51) Int. Cl.[7] ..... A01H 5/00
(52) U.S. Cl. ..... Plt./258
(58) Field of Search ..... Plt./258

(56) References Cited

U.S. PATENT DOCUMENTS

| | | | |
|---|---|---|---|
| PP6,000 P | 9/1987 | Christensen | Plt./130 |
| PP6,895 P | 7/1989 | Meilland | Plt./137 |
| 4,925,696 A | 5/1990 | Slimak | 426/637 |
| 5,034,327 A | 7/1991 | Takayama et al. | 435/240.4 |
| PP8,526 P | 12/1993 | Wilfret | Plt./373 |
| 5,464,646 A | 11/1995 | Huang et al. | 426/615 |
| PP10,466 P | 6/1998 | Wilfret | Plt./373 |

OTHER PUBLICATIONS de la Pena, R. S. The Univsersity of Hawaii Taro Germplasm Nursery and Breeding Program Proceedings of the Workshop on Taro and Tanier Modeling University of Hawaii Research Extension Series 136 pp. 7–9, Aug. 1992.*

Whitney, L. D. et al. Taro Varieties in Hawaii Agricultural Experiment Station Bulletin No. 84 pp. 1–86, Dec. 1939.*

* cited by examiner

*Primary Examiner*—Bruce R. Campell
*Assistant Examiner*—Wendy Baker
(74) *Attorney, Agent, or Firm*—Medleh & Carroll LLP

(57) ABSTRACT

The present invention relates to a new and distinct variety of *Colocasia esculenta* (popularly known as taro) named 'Pauakea'. 'Pauakea' differs distinctively from other taro plants by its unique combination of resistance to taro leaf blight caused by *Phytophthora colocasiae*, resistance to root rot caused by Pythium spp., vigorous growth, large mother corm size, and white corm of very good flour quality and good eating quality.

6 Drawing Sheets

The present invention relates to a new and distinct variety of *Colocasia esculenta* (popularly known as taro) named 'Pauakea'. 'Pauakea' plants were produced by cross-pollination of the commercial cultivars 'Ngeruuch' and 'Maui Lehua,' selection of progeny for a single plant which exhibited desirable agronomic and disease resistance properties, and asexual reproduction of the selected plant using tissue culture and propagation of hulis. 'Pauakea' differs distinctively from other taro plants by its unique combination of resistance to taro leaf blight (TLB) caused by *Phytophthora colocasiae*, resistance to root rot caused by Pythium spp., vigorous growth, large mother corm size, and white corm of very good flour quality and good eating quality.

REPRODUCTION

'Pauakea' is a product of the taro-breeding program of the University of Hawaii, Honolulu, Hi. The 'Pauakea' cultivar was derived from a single plant which was selected from a cross between the Hawaiian taro cultivar 'Maui Lehua' (unpatented) and the Palauan taro cultivar 'Ngeruuch' (unpatented; also referred to as 'P10'). Ancestry of both parents is unknown, except that 'Maui Lehua' belongs to the Group Lehua of Hawaiian-Polynesian taros and is susceptible to taro leaf blight (TLB), caused by *Phytophthora colocasiae*, and 'Ngeruuch' is a Micronesian taro from Palau and is highly resistant to this disease.

'Maui Lehua', the preferred poi taro of Hawaii, was selected as the female parent; 'Maui Lehua' exhibits the desirable agronomic characteristics of absence of runners, less than 6 suckers per plant, and superior poi quality purple corm. 'Ngeruuch' was selected as the pollen parent for its high resistance to the taro leaf blight disease; 'Ngeruuch' exhibits undesirable vegetative proliferation by long stolons. Both parents are commercial cultivars. The initial cross-pollination of 'Ngeruuch' pollen and 'Maui Lehua' female flowers was made to produce a new poi taro having the agronomic characteristics of 'Maui Lehua' and the resistance to TLB of 'Negeruuch.' $F_1$ progeny plants (including a single plant which was later designated 'Pauakea') were selected for their disease resistance to TLB, pocket rot, and basal rot, having fewer than 6 suckers and no runners, poi quality, and taste of cooked corms.

Asexual reproduction of 'Pauakea' was performed in Honolulu, Hi, by apical meristem multiplication using standard tissue culture procedures [Keolanui et al. (1993) Handbook for commercial-scale taro (*Colocasia esculenta*) tissue culture in Hawaii. University of Hawaii, College of Tropical Agriculture and Human Resources, Research Extension Series 145]. The traits of the plants which were generated by apical meristem multiplication were identical to those of the plant from which they were asexually reproduced. Cloned and rooted tissue culture plants of 'Pauakea' were produced at the University of Hawaii at Manoa, Honolulu, Hi.

Rooted tissue culture plants were grown to hulis to produce plants for field-testing as follows. Rooted tissue culture plants were transplanted from rooting medium to Sunshine Mix 4 potting soil. Potting mix (10 cubic inches volume) was used per plant in Compak® 606 multi-pots 3.25" deep with cell opening 2.25"×2" (T.O. Plastics Inc, 78th Street, MPLS, Minn. 55425). The Sunshine Mix 4 was mixed thoroughly with 2 lb of fast acting granular lime (The Chas H. Lilly Co, Portland, Oreg. 97283) and 0.5 lb of Osmocote slow release fertilizer 14-14-14 (Scotts-Sierra Horticultural Products Co., 14111 Scottslawn Rd., Marysville, Ohio 43042) per cublic yard prior to use. The cells were placed in T.O. Plastics trays without holes 20.25"×15.75"×2.5" in size, containing a liquid nutrient solution made with one teaspoon of Peters (Scotts-Sierra) all purpose soluble plant food 20-20-20/gallon of water. Plants were grown for 3–4months in a greenhouse at 28° C. until the stem base of the plants was one inch in diameter and the plants were ready for field planting.

Plants were also propagated in Hakalau, Hi., by the farming practice known as huli production whereby the apical shoots are separated from the rhizomes by cutting the shoot at the top of the corm immediately above the newest leaf scar and planted. A large number of plants of the new variety have been reproduced by this method and the resulting plants have exhibited the distinguishing characteristics of the original plant which was used for asexual propagation, indicating that the new 'Pauakea' cultivar is established.

CHARACTERISTICS

Figure 1:
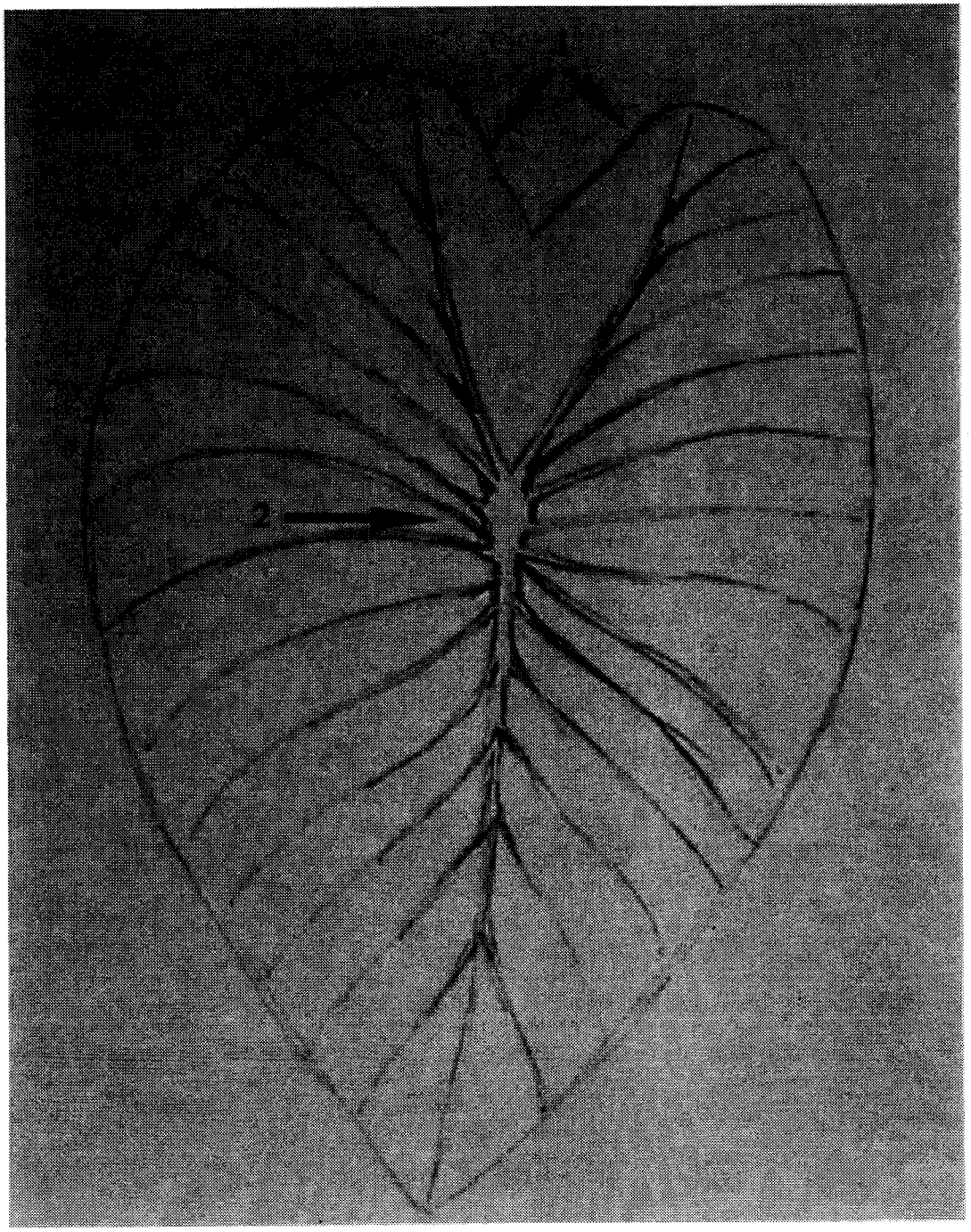
FIG. 1 is a diagram of a leaf which has been laid flat on a horizontal surface, showing the piko (2), i.e., point of attachment of petiole to the lamina, and the deep to acute angled sinus (1) between the lobes of the leaf on 'Pauakea'.

The asexually reproduced 'Pauakea' cultivar has several desirable horticultural characteristics, including resistance to taro leaf blight caused by *Phytophthora colocasiae*, resistance to root rot caused by Pythium spp., vigorous growth, large mother corm size, and white corm of very good flour quality and good eating quality. 'Pauakea' plants are suitable for both upland culture and wetland culture.

Resistance of 'Pauakea' to TLB was measured in field experiments at the Hakalau Farm and Nursery in Hamakua, Hi, which is located at a 600 ft elevation, receives high precipitation, and has a high incidence of TLB. Four subplots of 'Pauakea' were planted at 2 elevations at Hamakua, Hi. during April and May of 1998. Each subplot contained 4 rows spaced 4 ft apart with 10 plants/row at a distance of 2 ft between plants. A randomized plot design was used for these tests. Disease assessment consisted of a visual determination of the percent area of foliar TLB damage caused by *Phytophthora colocasiae*. This data is shown in Table 1.

TABLE 1

| | Percent area of Foliar Damage Caused by Phytophthora colocasiae[1] | | |
|---|---|---|---|
| Cultivar | First Experiment | Second Experiment | Third Experiment |
| 'Maui Lehua' | 0.2069 a | 0.2856 a | 0.2800 a |
| 'Pauakea' | 0.0342 bc | 0.1014 b | 0.0578 b |
| 'Ngeruuch' | 0.0153 c | 0.0320 d | 0.0194 b |

[1]Means with different letters are significantly different from one another. P ≦ 0.05 (Tukey's LSD test)

Table 1 shows that 'Pauakea' shows a significantly high degree of resistance to TLB which is similar to that exhibited by 'Ngeruuch' and which is much greater than that observed by 'Maui Lehua'. 'Pauakea' leaves show symptoms of hypersensitive reaction when affected by taro leaf blight disease.

Corm yield was also measured in plants planted and harvested at Hamakua, Hi. The mean yield of the main corm of 'Pauakea' and 'Maui Lehua' was 2.9000 pounds/plant (i.e., 22,678 pounds/acre) and 2.4458 pounds/plant (i.e., 19,126 pounds/acre), respectively, which was not a statistically significant difference using Tukey's LSD test.

'Pauakea' was resistant to root rot caused by Pythium spp., and showed no pocket rot, whereas 'Maui Lehua' was susceptible to root rot. The number of suckers (3-2) produced by 'Pauakea' was significantly lower than the number (5-4) produced by 'Ngeruuch'.

Poi quality was measured by determining the stickiness, smoothness, viscosity, taro aroma intensity, and sweetness of the steamed or boiled corm which had been ground and mixed with water to 20% total solids. Desirable poi quality characteristics include a smooth texture, sweet taste, a consistency similar to soft mashed potato, stickiness similar to tapioca pudding, and strong taro aroma. Poi produce from 'Pauakea' was greyish white (compared to purple when prepared from 'Maui Lehua') with good poi quality.

Eating quality was measured by determining the starchiness, and consistency of baked or boiled corms, with a starchy and moist consistency being desirable characteristics. Eating quality of 'Pauakea' corm was good.

Flour quality was measured by estimating the yield, consistency, and content of oxalic acid of flour prepared from raw taro. Desirable characteristics include high yield, and a consistency similar to commercial wheat flour, that when mixed with sufficient water forms a sticky dough which has a low content of oxalic acid (<0.07% ) and an agreeable sweet flavor. Flour prepared from 'Pauakea' was white with very good flour quality.

DETAILED BOTANICAL DESCRIPTION

The following combination of traits distinguishes 'Pauakea' as a new cultivar from other taro cultivars, including the parent plants from which it was derived. The photographs closely approximate the colors of the plants. However, to further facilitate the identification of color, reference is made to the British Colour Council and The Royal Horticultural Society, Horticultural Colour Chart, except where general color terms of ordinary dictionary significance are obvious. Wherein dimensions, sizes and other characteristics are given, it is to be understood that such characteristics are approximations of averages set forth as accurately as practicable. The descriptions herein are from 3 to 6 month old specimens grown in Hakalau, Hi. as indicated.

Plant: *Size.*—Vigorous plant with wide spread. The plant has 3–5 suckers closely attached to the mother plant and infrequently producing a sucker on a rhizome borne on a short stolon less than 2 decimeters long. A "mother plant" is the plant material which is first introduced into the soil to begin taro production and which gives rise to a corm, herein referred to as "mother corm". Typically, this plant material contains part of the huli and 2–3 leaf blades. The corm of the mother plant produces rhizomes which give rise to daughter plants which begin to appear above soil level at about 4–5 months after planting of the mother plant. Plant Size is up to a maximum of 1.60 m and 1.90 m high at 3 and 6 months after planting, respectively. The plant is slightly spreading. Main plant pseudo-stem circumference, at soil line, is up to 45 cm and 53 cm at 3 and 6 months after planting, respectively. Plants were grown on silicate clay soils, with average daily temperature of 27° C., average rainfall of 150 inches/year and average solar radiation of 450 langley (Cal/sq cm/day).

*Maturity.*—11 months from planting to harvest marketable corms.

*Quality.*—Flour quality 4.5 (scale of 1 to 5; 1=poor and 5=excellent). Poi quality 3.5 (scale same as above). Eating quality 3.5 (scale same as above).

Leaves:

*Number.*—Usually 4–10 month old mother plants maintain 6–7 functional leaves at a time, each new leaf is produced approximately every 10 days until the corm matures.

*Size.*—Leaves are up to 90 cm and 95 cm long, and up to 61 cm and 65 cm wide on 3- and 6-month old plants, respectively. Petioles are up to 150 cm long.

Figure 2:
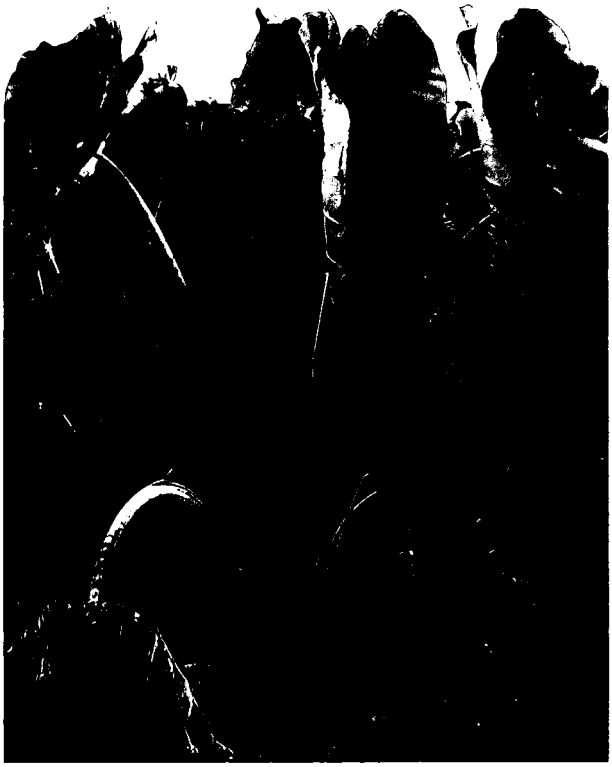
FIG. 2 is a photograph of slightly ovate sagittate 'Pauakea' leaf blade with a deep 70° to 80° acute angle sinus. Lamina is dark green with light-green venation, 38 cm wide by 78 cm long.
Figure 3:
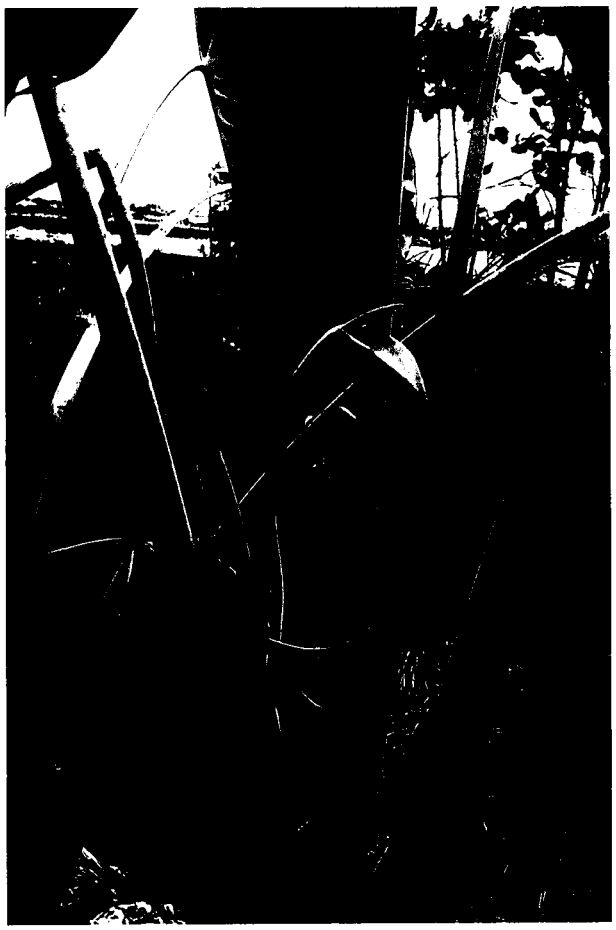
FIG. 3 is a photograph of the underside of a portion of 'Pauakea' leaf blade having light green petioles, up to 150 cm long. Inflorescence up to 100 cm tall, with a simple spadix subtended by a herbaceous spathe up to 45 cm long.
Figure 6:
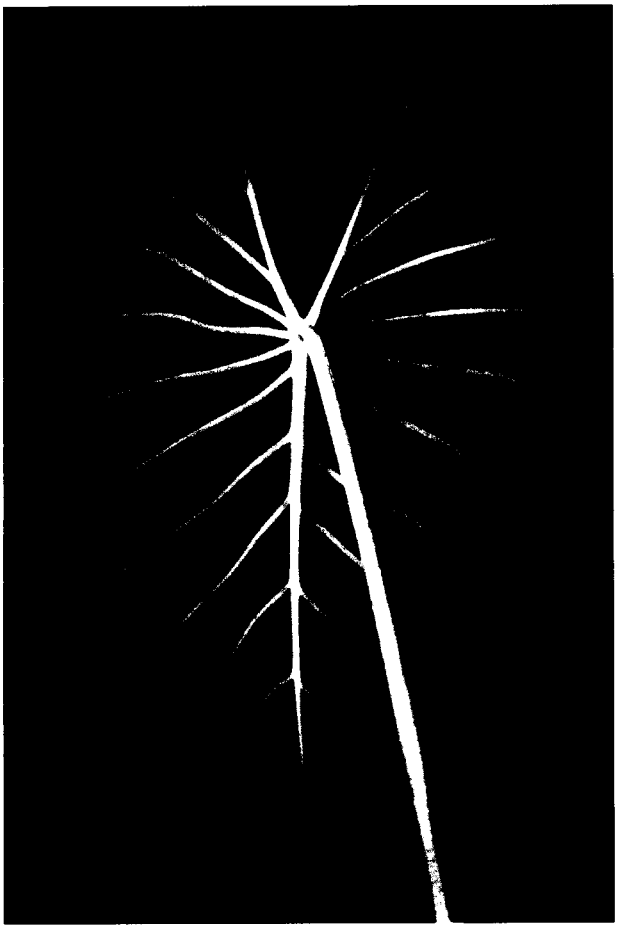
FIG. 6 is a photograph of the adaxial surface of a 'Pauakea' leaf from a 8-month old plant showing its light-green color and yellow green petiole and lighter green prominent leaf veins.

*Shape.*—Leaves are erect with the apex down, have sagittate, slightly ovate lamina with entire leaf margins, a deep 70° to 80° acute angle sinus between lobes, a large piko, peltate leaf base, pointed apex, open leaf sheath, and palmate-venation (FIG. 1 and FIG. 2). Lamina appendages are absent,

*Color.*—Leaves are flat dark green (R.H.S. # 137 A). Point of attachment of petiole to lamina (piko) on abaxial surface (FIG. 1) is colored light green (R.H.S. # 145 B). Petioles are pea green (R.H.S. # 145 C) up to 140 cm to 155 cm long with a sheath margin of the same color. Petiole sap colorless. Adaxial lamina (FIG. 6) color light green (R.H.S. #137 D) with light yellow-green veins (R.H.S. #145 D).

*Veins.*—Three principal veins radiating from the piko, the largest a midrib extending from the piko to the tip of the lamina with up to 10 pairs of secondary veins radiating from it (FIG. 1). The 2 shorter main veins extend from the piko to the tip of the lobes with 3 secondary veins each. Veins on the abaxial surface are light yellowish green (R.H.S. # 145 B) and on the adaxial surface are a shade lighter in color (R.H.S. # 145 D).

Corms:

*Size.*—Main corm is large measuring 16 cm to 18 cm long with a diameter up to 15 cm to 18.5 cm at the widest cross-section.

Figure 4:
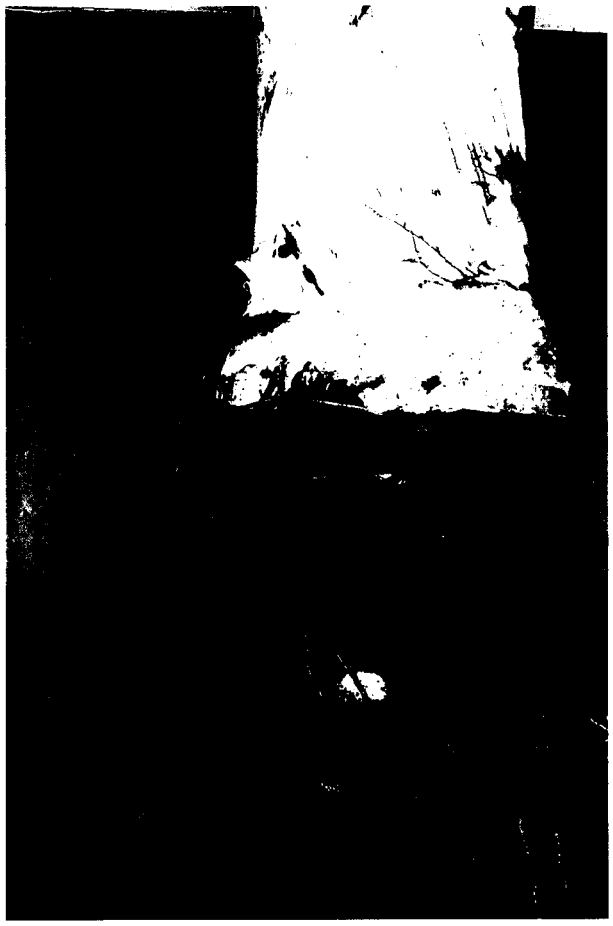
FIG. 4 is a photograph of a 'Pauakea' cannon ball shaped corm with light-brown skin and stout white roots.

*Shape.*—Cannon ball with stout white roots (FIG. 4). At 5 to 7 cm from the corm base there is a 1 cm deep depression 3–4 cm long which is the scar remaining from the point of attachment of the inflorescence.

Figure 5:
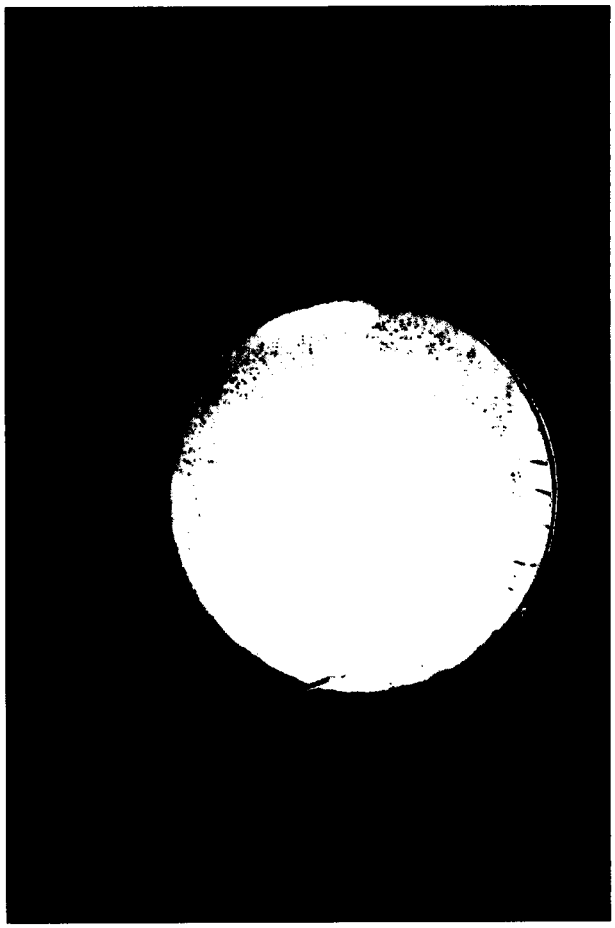
FIG. 5 is a photograph of a cross section of a 'Pauakea' corm showing creamy-white flesh.

*Color.*—Outer skin tissue at base of corm is garnet-brown (R.H.S. # 200 A), upper corm skin tissue toward the apex is orange-brown (R.H.S. # 164 B). Corm flesh is creamy-white (R.H.S. # 155D) with corm fibers of the same creamy-white color (FIG. 5).

*Weight.*—Rhizome weight of the 'Pauakea' mother plant is from 1.8 to 3.8 kg.

Rhizomes: The mother corm produces 3 to 5 suckers on closely attached rhizomes or on 1–2 decimeter long slender rhizomes approxiamtely 4–5 months after planting the huli. Closely attached rhizomes give rise to daughter plants. The daughter plant corms weigh 0.3 to 0.9 kg at harvest. The outer skin tissue of the daughter corm is garnet-brown (R.H.S. #200 A) and upper leaf scars are orange-brown (R.H.S.#164 B). Flesh of daughter plant corm on cross-section is creamy-white (R.H.S. # 155D).

Inflorescence: Profusely produced during August, up to 100 cm tall, with a simple spadix subtended by a herbaceous keeled spathe 36 to 45 cm long. The lower tubular portion of the spathe is 6 cm to 7 cm long and is light pea green (R.H.S. # 145 B). At the base of the spathe there is a red-purple (R.H.S. # 71 A) spot on both sides. The upper portion of the spathe is partially open and droopy, yellow-orange (R.H.S. # 11 A) and 26 cm to 39 cm long, the spadix is 11 to 14 cm long having at the base a 3–4 cm light green (R.H.S. # 137 C) portion producing the female inflorescence, next is 2–3 cm white sterile tissue, followed by 3–5 cm of yellow-orange (R.H.S. # 14 C) exposed male flowers, and a yellow-orange (R.H.S. # 14 C) sterile appendage 2 cm long. The peduncle is pale green (R.H.S. # 145 A), 64 cm to 90 cm long. The stigma is receptive approximately 3 days after pollen dehiscence. The pollen is yellow orange (R.H.S. # 14 A). The fruit is a berry. Pollination has not been observed to occur naturally, fruit or seeds have not been observed.

The present invention relates to a new and distinct variety of *Colocasia esculenta* (popularly known as taro) named 'Pauakea'. 'Pauakea' differs distinctively from other taro plants by its unique combination of resistance to taro leaf blight caused by *Pytophthora colocasiae*, resistance to root rot caused by Pythium spp., vigorous growth, large mother corm size, and white corm of very good flour quality and good eating quality.

I claim:

1. A new and distinct variety of taro plant, substantially as illustrated and described herein, that is characterized by resistance to taro leaf blight caused by *Phytophthora colocasiae*, resistance to root rot caused by Pythium spp., vigorous growth, large mother corm size, and white corm of very good flour quality and good eating quality.

* * * * *